United States Patent [19]

Kahn

[11] Patent Number: 5,929,237
[45] Date of Patent: Jul. 27, 1999

[54] REVERSE-TURN MIMETICS AND METHODS RELATING THERETO

[75] Inventor: Michael Kahn, Kirkland, Wash.

[73] Assignee: Molecumetics Ltd., Bellevue, Wash.

[21] Appl. No.: 08/549,007

[22] Filed: Oct. 27, 1995

[51] Int. Cl.[6] .................... C07D 471/00; C07D 487/00; G01N 33/543
[52] U.S. Cl. .......................................... 544/279
[58] Field of Search .................... 435/7.1; 530/317, 530/323, 333; 436/518; 544/1, 47, 48, 224, 233, 235, 236, 238, 239, 242, 244, 278, 279, 282, 295, 247, 253, 298, 336; 540/484, 485, 492, 500, 502, 506, 507, 510, 525

[56] References Cited

U.S. PATENT DOCUMENTS

| | | | |
|---|---|---|---|
| 5,440,013 | 8/1995 | Kahn | 530/317 |
| 5,545,568 | 8/1996 | Ellman | 436/518 |

FOREIGN PATENT DOCUMENTS

| | | |
|---|---|---|
| WO 94/03494 | 2/1994 | WIPO . |
| WO 97/15557 | 5/1997 | WIPO . |

OTHER PUBLICATIONS

Lam et al., Nature. vol. 354. pp. 82–84, Nov. 7, 1991.
Sauter et al., "Novel basically substituted pyrimidines and benzothienopyrimidines," Chemical Abstracts Database, Accession No. 87:84931, 1977.
Gatta et al., "New [f]–fused xanthines: synthesis of 1,3–dipropyl–1H,3H–pyrazino, pyrido, pyrimido and pyrrole [2,1–f]purine–2,4–diones, " Chemical Abstracts Database: 121:57444, 1994.
Okawara et al., "Preparation and hydrogenolysis of fused piperazines by reaction of diamine and triamine derivatives with benzil. Applications to the synthesis of terminal N–monoprotected triamines," Chemical Abstracts Database, Accession No. 117:191810 1992.
Kappe and Kappe, "Cross–conjugated and pseudo–cross–conjugated mesomeric betaines. XVIII. Bicyclic mesoionic pyrimidines with cardiovascular activity," Chemical Abstracts Database, Accession No. 116:83634, 1992.
Dennin et al., "Synthesis of derivatives of pyrazino[1,2-a]pyrimidin-4-ones," Chemical Abstracts Database, Accession No. 114:164135, 1991.
Okawara et al., "Simple preparation of terminal N–monoprotected triamines using fused piperazines," Chemical Abstracts Database, Accession No. 114:101300, 1991.
Abignente et al., "Research on heterocyclic compounds. XVI. 2–Methylimidazo[1,2-a]pyrazine-3-carboxylic acids," Chemical Abstracts Database, Accession No. 103:87841, 1985.
Penn et al., "Glyantrypine, a novel anthranilic acid–containing metabolite of *Aspergillus clavatus*," Chemical Abstracts Database, Accession No. 117:127875, 1992.
Penn et al., "Biosynthesis of glyantrypine by *Aspergillus clavatus*," Chemical Abstracts Database, Accession No. 117:44249, 1992.
Cutler et al., "Cinereain: a novel metabolite with plant growth regulating properties from *Botrytis cinerea*, " Chemical Abstracts Database, Accession No. 109:165645, 1988.
Tanaka and Narita, "Synthesis of pyrido[2,3–b]pyrazine derivatives," Chemical Abstracts Database, Accession No. 84:31002, 1975.
Pinnen et al., "Cyclization under mild conditions of anthraniloyl and N–methylanthraniloyl dipeptides," Chemical Abstracts Database, Accession No. 110:76029, 1989.
Rothe et al., "Secondary all–L–cyclotripeptides," Chemical Abstracts Database, Accession No. 103:215766, 1985.
Pinnen et al., "Ten–membered cyclotripeptides: influence of the ring–flexibility on intramolecular reactions," Chemical Abstracts Database, Accession No. 102:132448, 1985.
Faehnle and Rothe, "Syntheses and reactions of peptide cyclols," Chemical Abstracts Database, Accession No. 102:7061, 1985.
Lucente et al., "Synthesis and x–ray crystal structure of a tripeptidic cyclol," Chemical Abstracts Database, Accession No. 96:69410, 1982.
Rothe et al., "Cyclol formation during tripeptide cyclizations. Synthesis of a secondary cyclotripeptide, cyclo–(D–Phe–L–Pro–L–Pro)," Chemical Abstracts Database, Accession No. 97:56231, 1982.
Kadam et al., "Fermentative manufacture of multiple drup resistance–attenuating ardeemins," Chemical Abstracts Database, Accession No. 121:7435, 1994.
Barrow et al., "Spiroquinazoline, a novel substance P inhibitor with a new carbon skeleton, isolated from *Aspergillus flavipes*," Chemical Abstracts Database, Accession No. 121:129499, 1994.
Numata et al., "Structures of cytotoxic substances and new quinazoline derivatives produced by a fungus from a saltwater fish," Chemical Abstracts Database, Accession No. 116:210833, 1992.

*Primary Examiner*—Ponnathapura Achutamurthy
*Assistant Examiner*—P. Ponnaluri
*Attorney, Agent, or Firm*—Seed and Berry LLP

[57] ABSTRACT

Conformationally constrained compounds which mimic the secondary structure of reverse-turn regions of biologically active peptides and proteins are disclosed. Such reverse-turn mimetics have utility over a wide range of fields, including use as diagnostic and therapeutic agents. Libraries containing the reverse-turn mimetics of this invention are also disclosed, as well as methods for screening the same to identify biologically active members.

14 Claims, 1 Drawing Sheet

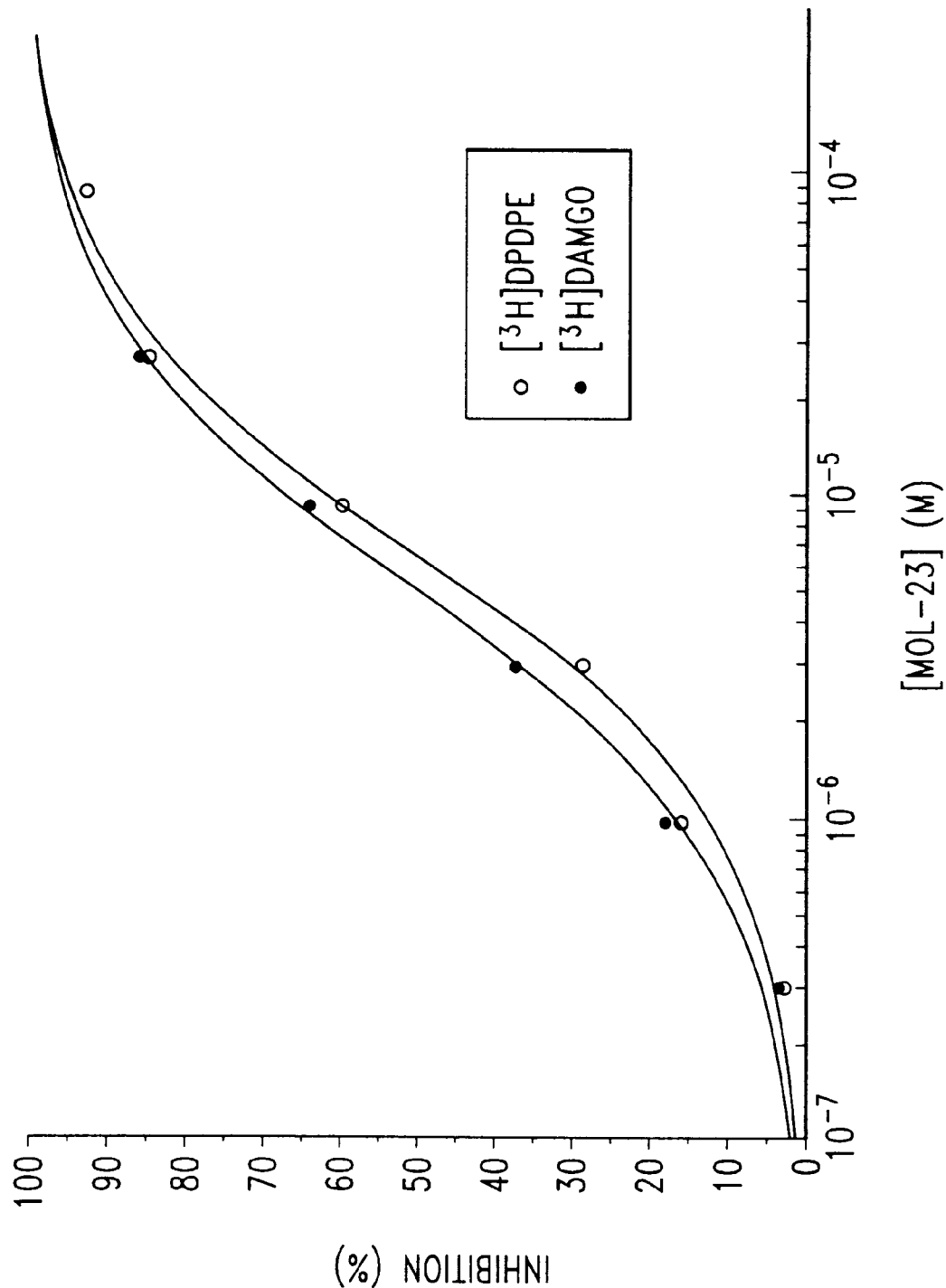

REVERSE-TURN MIMETICS AND METHODS RELATING THERETO

TECHNICAL FIELD

The present invention relates generally to reverse-turn mimetics and to a chemical library of reverse-turn mimetics.

BACKGROUND OF THE INVENTION

Random screening of molecules for possible activity as therapeutic agents has occurred for many years and resulted in a number of important drug discoveries. While advances in molecular biology and computational chemistry have led to increased interest in what has been termed "rational drug design," such techniques have not proven as fast or reliable as initially predicted. Thus, in recent years there has been a renewed interest and return to random drug screening. To this end, particular strides having been made in new technologies based on the development of combinatorial chemistry libraries, and the screening of such libraries in search for biologically active members.

In general, combinatorial chemistry libraries are simply a collection of molecules. Such libraries vary by the chemical species within the library, as well as the methods employed to both generate the library members and identify which members interact with biological targets of interest. While this field is still young, methods for generating and screening libraries have already become quite diverse and sophisticated. For example, a recent review of various combinatorial chemical libraries has identified a number of such techniques, including the use of both tagged and untagged library members (Janda, *Proc. Natl. Acad. Sci. USA* 91:10779–10785, 1994).

To date, combinatorial chemistry libraries have generally been limited to members of peptide or nucleotide origin. To this end, the techniques of Houghten et al. illustrate an example of what is term a "dual-defined iterative" method to assemble soluble combinatorial peptide libraries via split synthesis techniques (*Nature* (London) 354:84–86, 1991; *Biotechniques* 13:412–421, 1992; *Bioorg. Med. Chem. Lett.* 3:405–412, 1993). By this technique, soluble peptide libraries containing tens of millions of members have been obtained. Such libraries have been shown to be effective in the identification of opioid peptides, such as methionine- and leucine-enkephalin (Dooley and Houghten, *Life Sci.* 52, 1509–1517, 1993), and a N-acylated peptide library has been used to identify acetalins, which are potent opioid antagonists (Dooley et al., *Proc. Natl. Acad. Sci. USA* 90:10811–10815, 1993. More recently, an all D-amino acid opioid peptide library has been constructed and screened for analgesic activity against the mu ("μ") opioid receptor (Dooley et al, *Science* 266:2019–2022, 1994).

While combinatorial libraries containing members of peptide and nucleotide origin are of significant value, there is still a need in the art for libraries containing members of different origin. For example, traditional peptide libraries to a large extent merely vary the amino acid sequence to generate library members. While it is well recognized that the secondary structures of peptides are important to biological activity, such peptide libraries do not impart a constrained secondary structure to its library members.

To this end, some researchers have cyclized peptides with disulfide bridges in an attempt to provide a more constrained secondary structure (Tumelty et al., *J. Chem. Soc.* 1067–68, 1994; Eichler et al., *Peptide Res.* 7:300–306, 1994). However, such cyclized peptides are generally still quite flexible and are poorly bioavailable, and thus have met with only limited success.

More recently, non-peptide compounds have been developed which more closely mimic the secondary structure of reverse-turns found in biologically active proteins or peptides. For example, U.S. Pat. No. 5,440,013 to Kahn and published PCT WO94/03494 to Kahn both disclose conformationally constrained, non-peptidic compounds which mimic the three-dimensional structure of reverse-turns.

While significant advances have been made in the synthesis and identification of conformationally constrained, reverse-turn mimetics, there is still a need in the art for small molecules which mimic the secondary structure of peptides. There is also a need in the art for libraries containing such members, as well as techniques for synthesizing and screening the library members against targets of interest, particularly biological targets, to identify bioactive library members. The present invention fulfills these needs, and provides further related advantages.

SUMMARY OF THE INVENTION

In brief, the present invention is directed to conformationally constrained compounds which mimic the secondary structure of reverse-turn regions of biologically active peptides and proteins. This invention also discloses libraries containing such compounds, as well as the synthesis and screening thereof.

The compounds of the present invention have the following general structure (I):

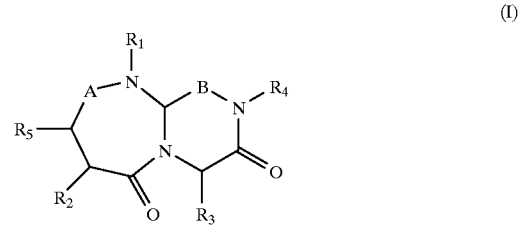

(I)

wherein A is —(CHR')$_n$— and B is —(CHR")$_m$— where n=0, 1 or 2 and m=1, 2 or 3; and wherein R', R", R$_1$, R$_2$, R$_3$, R$_4$ and R$_5$ are as defined in the following detailed description.

In one embodiment, n=0, R" and R$_5$ are hydrogen, and the compounds of this invention have the following structure (Ia):

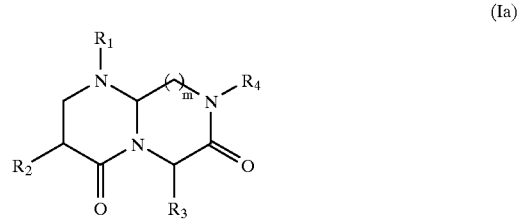

(Ia)

wherein m=1, 2 or 3 and R$_1$, R$_2$, R$_3$ and R$_4$ are as defined in the following detailed description.

In a further embodiment, n=0, R" and R$_5$ are hydrogen, m=1, and the compounds of the present invention have the following structure (Ib):

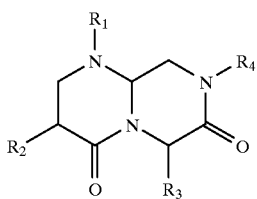

(Ib)

wherein $R_1$, $R_2$, $R_3$ and $R_4$ are as defined in the following detailed description.

The present invention is also directed to libraries containing compounds of structure (I) above, as well as methods for synthesizing such libraries and methods for screening the same to identify biologically active compounds.

These and other aspects of this invention will be apparent upon reference to the attached figures and following detailed description. To this end, various references are set forth herein which describe in more detail certain procedures, compounds and/or compositions, and are incorporated by reference in their entirety.

BRIEF DESCRIPTION OF THE DRAWING

FIG. 1 illustrates the percent inhibition of radioligand binding to δ and μ opiate receptors of a representative reverse-turn mimetic of this invention as a function of concentration.

DETAILED DESCRIPTION OF THE INVENTION

The present invention is directed to reverse-turn mimetics and chemical libraries containing reverse-turn mimetics. The reverse-turn mimetics of the present invention are useful as bioactive agents, including (but not limited to) use as diagnostic, prophylactic and/or therapeutic agents. The reverse-turn mimetic libraries of this invention are useful in the identification of such bioactive agents. In the practice of the present invention, the libraries may contain from tens to hundreds to thousands (or greater) of individual reverse-turn mimetics (also referred to herein as "members").

In one aspect of the present invention, a reverse-turn mimetic is disclosed having the following structure (I):

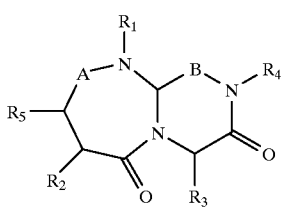

(I)

where A is —(CHR)$_n$—, and B is —(CHR')$_m$—, n=0, 1 or 2 and m=1, 2 or 3; and where R', R", $R_1$, $R_2$, $R_3$, $R_4$ and $R_5$ are as defined below.

In structure (I) above, the solid line designation for attachment of $R_2$, $R_3$, and $R_5$ indicates that these R groups may lie either above or below the plane of the page. If a reverse-turn mimetic of this invention is intended to mimic a reverse-turn of naturally occurring amino acids (i.e., "L-amino acids"), the R groups would generally lie below the plane of the page (i.e., "R") in Structure (I). However, if the reverse-turn mimetic of this invention is intended to mimic a reverse-turn containing one or more D-amino acids, then the corresponding R group or groups would lie above the plane of the page (i.e., "R") in Structure (I).

In one embodiment, $R_1$ and $R_4$ are the same or different and represent the remainder of the compound, and R', R", $R_2$, $R_3$, and $R_5$ are the same or different and independently selected from an amino acid side chain moiety or derivative thereof. With regard to R' and R", it should be understood that each occurrence of R' and R" is independently selected from amino acid side chain moieties or derivatives thereof. For example, when m=2, B is a —CHR"CHR"— moiety. In this instance, both occurrences of R" are independently selected, and may be the same or different. Thus, if the first occurrence of R" is hydrogen and the second methyl, B would have the structure —CH$_2$CH(CH$_3$)—.

As used herein, the term "remainder of the compound" means any moiety, agent, compound, support, molecule, linker, amino acid, peptide or protein covalently attached to the reverse-turn mimetic at either the $R_1$ and/or $R_4$ positions. This term also includes amino acid side chain moieties and derivatives thereof.

As used herein, the term "amino acid side chain moiety" represents any amino acid side chain moiety present in naturally occurring proteins including (but not limited to) the naturally occurring amino acid side chain moieties identified in Table 1. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine.

TABLE 1

Amino Acid Side Chain Moieties

| Amino Acid Side Chain Moiety | Amino Acid |
|---|---|
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3^+$ | Lysine |
| —(CH$_2$)$_3$NHC(NH$_2$)NH$_2^+$ | Arginine |
| —CH$_2$-[imidazole] | Histidine |
| —CH$_2$COO$^-$ | Aspartic acid |
| —CH$_2$CH$_2$COO$^-$ | Glutamic acid |
| —CH$_2$CONH$_2$ | Asparagine |
| —CH$_2$CH$_2$CONH$_2$ | Glutamine |
| —CH$_2$-[phenyl] | Phenylalanine |
| —CH$_2$-[phenyl]-OH | Tyrosine |

TABLE 1-continued

Amino Acid Side Chain Moieties

| Amino Acid Side Chain Moiety | Amino Acid |
|---|---|
| 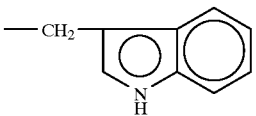 | Tryptophan |
| —CH₂SH<br>—CH₂CH₂SCH₃<br>—CH₂OH<br>—CH(OH)CH₃ | Cysteine<br>Methionine<br>Serine<br>Threonine |
|  | Proline |
| 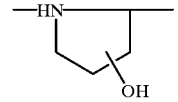 | Hydroxyproline |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and phenylalanine may generally be classified as lower chain alkyl, aryl, or aralkyl moieties. Derivatives of amino acid side chain moieties include other straight chain or branched, cyclic or noncyclic, substituted or unsubstituted, saturated or unsaturated lower chain alkyl, aryl or aralkyl moieties.

As used herein, "lower chain alkyl moieties" contain from 1–12 carbon atoms, "lower chain aryl moieties" contain from 6–12 carbon atoms and "lower chain aralkyl moieties" contain from 7–12 carbon atoms. Thus, in one embodiment, the amino acid side chain derivative is selected from a $C_{1-12}$ alkyl, a $C_{6-12}$ aryl and a $C_{7-12}$ aralkyl, and in a more preferred embodiment, from a $C_{1-7}$ alkyl, a $C_{6-10}$ aryl and a $C_{7-11}$ aralkyl.

Amino side chain derivatives of this invention further include substituted derivatives of lower chain alkyl, aryl, and aralkyl moieties, wherein the substituent is selected from (but are not limited to) one or more of the following chemical moieties: —OH, —OR, —COOH, —COOR, —CONH₂, —NH₂, —NHR, —NRR, —SH, —SR, —SO₂R, —SO₂H, —SOR and halogen (including F, Cl, Br and I), wherein each occurrence of R is independently selected from a lower chain alkyl, aryl and aralkyl moieties. Moreover, cyclic lower chain alkyl, aryl and aralkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

In a further embodiment, and in addition to being an amino acid side chain moiety or derivative thereof, or the remainder of the compound in the case of $R_1$ and $R_4$, $R_1$, $R_2$, $R_3$, $R_4$, or $R_5$ may be a linker facilitating the linkage of the compound to another moiety or compound. For example, the compounds of this invention may be linked to one or more known compounds, such as biotin, for use in diagnostic or screening assay. Furthermore, $R_1$, $R_2$, $R_3$, $R_4$ or $R_5$ may be a linker joining the compound to a solid support (such as a support used in solid phase peptide synthesis) or alternatively, may be the support itself. In this embodiment, linkage to another moiety or compound, or to a solid support, is preferable at the $R_1$ or $R_4$ position, and more preferably at the $R_4$ position.

In a preferred embodiment, $R_5$ is hydrogen.

In one embodiment of this invention, n=0, R" is hydrogen, and $R_5$ is hydrogen, and the reverse-turn mimetic has the following structure (Ia):

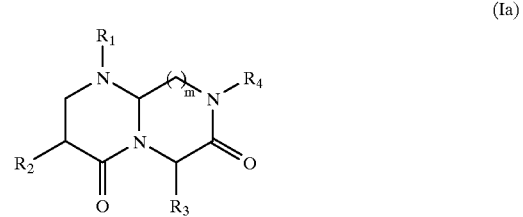

(Ia)

wherein m=1, 2 or 3 and $R_1$, $R_2$, $R_3$ and $R_4$ are as defined above. In a preferred embodiment, m=1 or 2, $R_1$ and $R_4$ represent the remainder of the compound, and $R_2$ and $R_3$ are individually selected from an amino acid side chain moiety.

In another embodiment, n=0, m=1, R" is hydrogen and $R_5$ is hydrogen, and the reverse-turn mimetic has the following structure (Ib):

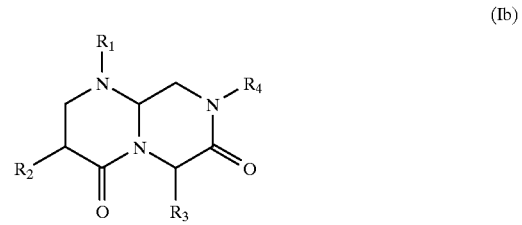

(Ib)

wherein $R_1$, $R_2$, $R_3$ and $R_4$ are as defined above. In a preferred embodiment, $R_1$ and $R_4$ represent the remainder of the compound, and $R_2$ and $R_3$ are independently selected from an amino acid side chain moiety.

The reverse-turn mimetics of the present invention may be prepared by utilizing appropriate starting component molecules (hereinafter referred to as "component pieces"). Briefly, first and second component pieces are coupled to form a combined first-second intermediate, third and fourth component pieces are coupled to form a combined third-fourth intermediate (or, if commercially available, a single third intermediate may be used), the combined first-second intermediate and third-fourth intermediate (or third intermediate) are then coupled to provide a first-second-third-fourth intermediate (or first-second-third intermediate) which is cyclized to yield the reverse-turn mimetics of thisinvention. Alternatively, the reverse-turn mimetics may be prepared by sequential coupling of the individual component pieces either stepwise in solution or by solid phase synthesis as commonly practiced in solid phase peptide synthesis.

Within the context of the present invention, a "first component piece" has the following structure 1:

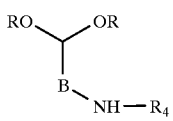

where $R_4$ and B are as defined above, and R is a protective group suitable for use in peptide synthesis. Suitable R groups include alkyl groups and, in a preferred embodiment, R is a methyl group. Such first component pieces may be readily synthesized by reductive amination by mating $CH(OR)_2—(CH_2)m—CHO$ with $H_2N—R_4$, or by displacement from $CH(OR)_2—(CH_2)m—Br$.

A "second component piece" of this invention has the following structure 2:

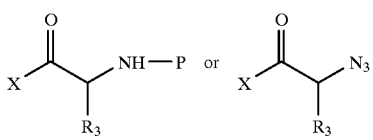

where $R_3$ is as defined above, P is an amino protective group suitable for use in peptide synthesis, and X represents the leaving group of the activated carboxylic acid group. Preferred protective groups include t-butyl dimethylsilyl (TBDMS), BOC, FMOC, and Alloc (allyloxycarbonyl). N-Protected amino acids are commercially available. For example, FMOC amino acids are available from a variety of sources. The conversion of these compounds to the second component pieces of this invention may be readily achieved by activation of the carboxylic acid group of the N-protected amino acid. Suitable activated carboxylic acid groups include acid halides where X is a halide such as chloride or bromide, acid anhydrides where X is an acyl group such as acetyl, reactive esters such as an N-hydroxysuccinimide esters and pentafluorophenyl esters, and other activated intermediates such as the active intermediate formed in a coupling reaction using a carbodiimide such as dicyclohexylcarbodiimide (DCC).

In the case of the azido derivative of an amino acid serving as the second component piece, such compounds may be prepared from the corresponding amino acid by the reaction disclosed by Zaloom et al. (*J. Org. Chem.* 46:5173–76, 1981).

A "third component piece" of this invention has the following structure 3:

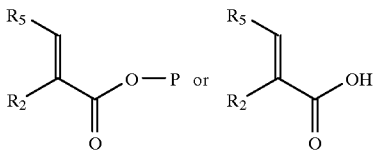

where $R_2$ and $R_5$ are as defined above, and P is a carboxylic acid protective group such as a methyl or t-butyl group. A "fourth component piece" of this invention has the following structure 4:

where $R_1$ is as defined above. Suitable fourth component pieces are commercially available from a variety of sources.

Alternatively, the fourth component pieces may be readily prepared by standard organic synthetic techniques commonly utilized for the synthesis of primary amines.

More specifically, the reverse-turn mimetics of this invention (see structure I above) are synthesized by reacting a first component piece with a second component piece to yield a combined first-second intermediate, followed by either reacting the combined first-second intermediate with third and fourth component pieces sequentially, or reacting the intermediate with a combined third-fourth intermediate to provide a combined first-second-third-fourth intermediate, and then cyclizing this intermediate to yield the reverse-turn mimetic.

The general synthesis of a reverse-turn mimetic having structure I may be synthesized by the following technique. A first component piece 1 is coupled to a second component piece 2 to yield, after N-deprotection, a combined first-second intermediate 1-2 as illustrated below:

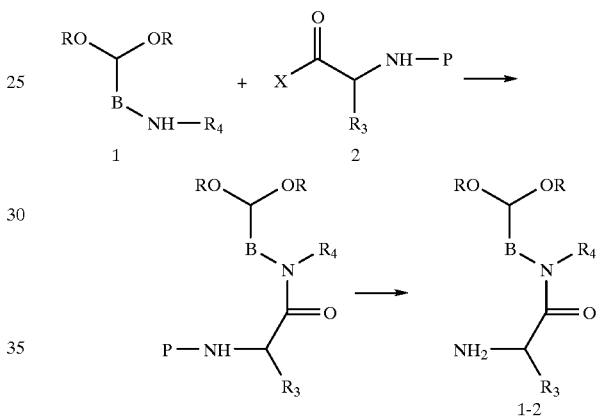

The synthesis of the reverse-turn mimetic may be convergent, in which case a combined third-fourth intermediate 3-4 is prepared from the coupling of a third component piece 3 with a fourth component piece 4 to yield, after O-deprotection, a combined third-fourth intermediate 3-4 as illustrated below:

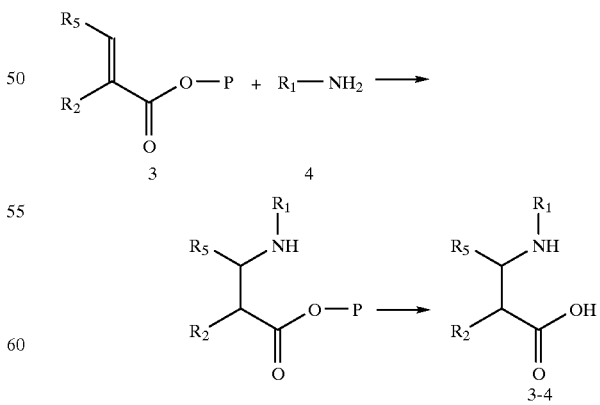

In the case where n of structure (I) above is 1 or 2, an intermediate of the following structure 3-4' can be made as follows:

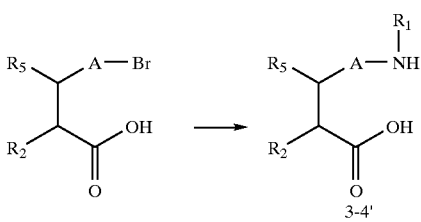

wherein A is —(CHR')$_n$—. Intermediate 3-4' may then be employed in place of intermediate 3-4 in the following reactions to yield a reverse-turn mimetic of this invention having structure (I).

Coupling of the combined intermediates 1-2 and 3-4 provides intermediate 1-2-3-4 which, upon cyclization, yield the reverse-turn mimetic (I) as illustrated below:

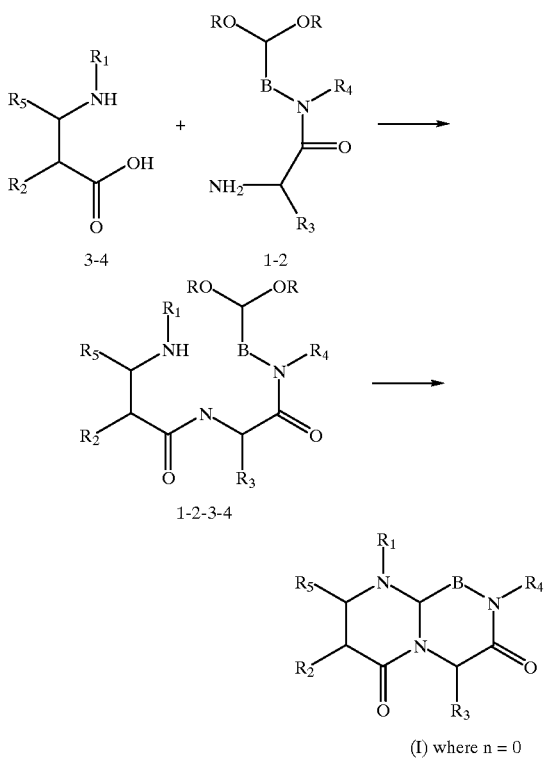

The syntheses of representative component pieces of this invention are described in Example 1. The syntheses of representative combined first-second and third-fourth intermediates are described in Examples 2 and 3, respectively. The coupling of these intermediates to form a representative combined first-second-third-fourth intermediate is described in Example 4. The cyclization of this intermediate to form a representative reverse-turn mimetic is described in Example 5.

As mentioned above, the reverse-turn mimetics of the present invention are useful as bioactive agents, such as diagnostic, prophylactic, and therapeutic agents. The opiate receptor binding activity of a representative reverse-turn mimetic is presented in Example 7. In this example, the reverse-turn mimetic was found to effectively inhibit the binding of a radiolabeled enkephalin derivative to the δ and μ opiate receptors. The data demonstrates the utility of these reverse-turn mimetics as receptor antagonists and as potential analgesic agents.

In another aspect of this invention, libraries containing reverse-turn mimetics of the present invention are disclosed. Once assembled, the libraries of the present invention may be screened to identify individual members having bioactivity. Such screening of the libraries for bioactive members may involve, for example, evaluating the binding activity of the members of the library or evaluating the effect the library members have on a functional assay. Screening is normally accomplished by contacting the library members (or a subset of library members) with a target of interest, such as, for example, an antibody, enzyme, receptor or cell line. Library members which are capable of interacting with the target of interest are referred to herein as "bioactive library members" or "bioactive mimetics". For example, a bioactive mimetic may be a library member which is capable of binding to an antibody or receptor, which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields reverse-turn mimetics which are themselves biologically active, and thus useful as diagnostic, prophylactic or therapeutic agents, and may further be used to significantly advance identification of lead compounds in these fields.

Synthesis of the peptide mimetics of the library of the present invention may be accomplished using known peptide synthesis techniques, in combination with the first, second and third component pieces of this invention. More specifically, any amino acid sequence may be added to the N-terminal and/or C-terminal of the conformationally constrained reverse-turn mimetic. To this end, the mimetics may be synthesized on a solid support (such as PAM resin) by known techniques (see, e.g., John M. Stewart and Janis D. Young, *Solid Phase Peptide Synthesis*, 1984, Pierce Chemical Comp., Rockford, Ill.) or on a silyl-linked resin by alcohol attachment (see Randolph et al., *J. Am Chem. Soc.* 117:5712–14, 1995).

In addition, a combination of both solution and solid phase synthesis techniques may be utilized to synthesize the peptide mimetics of this invention. For example, a solid support may be utilized to synthesize the linear peptide sequence up to the point that the conformationally constrained reverse-turn is added to the sequence. A suitable conformationally constrained reverse-turn mimetic which has been previously synthesized by solution synthesis techniques may then be added as the next "amino acid" to the solid phase synthesis (i.e., the conformationally constrained reverse-turn mimetic, which has both an N-terminus and a C-terminus, may be utilized as the next amino acid to be added to the linear peptide). Upon incorporation of the conformationally constrained reverse-turn mimetic into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained reverse-turn mimetic in solution using known solution coupling techniques.

In another aspect of this invention, methods for constructing the libraries are disclosed. Traditional combinatorial chemistry techniques (see, e.g., Gallop et al., *J. Med. Chem.* 37:1233–1251, 1994) permit a vast number of compounds to be rapidly prepared by the sequential combination of reagents to a basic molecular scaffold. Combinatorial techniques have been used to construct peptide libraries derived from the naturally occurring amino acids. For example, by taking 20 mixtures of 20 suitably protected and different amino acids and coupling each with one of the 20 amino acids, a library of 400 (i.e., $20^2$) dipeptides is created. Repeating the procedure seven times results in the preparation of a peptide library comprised of about 26 billion (i.e., $20^8$) octapeptides.

In a further aspect of this invention, methods for screening the libraries for bioactivity and isolating bioactive library members are disclosed. The libraries of the present invention may be screened for bioactivity by a variety of techniques and methods. Generally, the screening assay may be performed by (1) contacting a library with a biological target of interest, such as a receptor, and allowing binding to occur between the mimetics of the library and the target, and (2) detecting the binding event by an appropriate assay, such as by the colorimetric assay disclosed by Lam et al. (*Nature* 354:82–84, 1991) or Griminski et al. (*Biotechnology* 12:1008–1011, 1994) (both of which are incorporated herein by reference). In a preferred embodiment, the library members are in solution and the target is immobilized on a solid phase. Alternatively, the library may be immobilized on a solid phase and may be probed by contacting it with the target in solution.

The following examples are provided for purposes of illustration, not limitation.

EXAMPLES

Example 1

Synthesis of Component Pieces

In this example, the synthesis of representative component pieces which may be combined to form the reverse-turn mimetics of the present invention is disclosed.

A. Representative First Component Pieces

A first component piece having the following structure 1 was utilized:

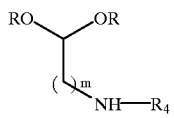

1 where $R_4$ is as defined above, and R represents a protective group suitable for use in peptide synthesis. Suitable R groups include alkyl groups and, in a preferred embodiment, R is a methyl group.

Generally, the first component piece is prepared by N-alkylation of an amine with a dialkylacetal of a 2-haloethanal. The synthesis of a representative first component piece from phenethylamine and the dimethylacetal of 2-bromoethanal is depicted schematically below.

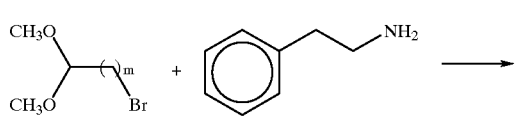

1a

-continued

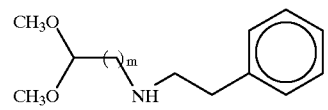

In the procedure, 24 ml (3.43 ml, 20.3 mmol) of bromide and 2.8 ml (2.71 g. 22.3 mmol) phenethylamine was added 40 ml freshly distilled THF in a 150 ml argon charged round-bottom flask equipped with a reflux condenser. The reaction was heated at a gentle reflux for 24 hours, then volatiles were removed under reduced pressure and the residue was dissolved in 200 ml dichloromethane. The organic layer was washed with 2×100 ml sat. aq. sodium bicarbonate, sat. aq. sodium chloride, and dried over anhydrous sodium sulfate. Volatiles were removed under reduced pressure and the residue dried for 3 hrs. under high vacuum to yield 3.5 g (83%) first component piece 1a (m=1) as a light brown oil used without further purification.

B. Representative Second Component Pieces

A representative second component piece of this invention is a reactive N-protected amino acid having an activated carboxylic acid group, or an azido derivative of an amino acid, as represented by the following structure 2:

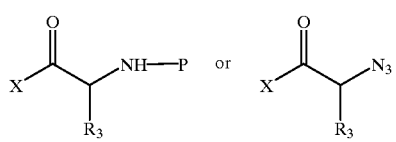

2 where $R_3$ is as defined above, P is an amino protective group suitable for use in peptide synthesis, and X represents the leaving group of the activated carboxylic acid group. Preferred protective groups include t-butyl dimethylsilyl (TBDMS), BOC, FMOC, and Alloc (allyloxycarbonyl). N-Protected amino acids are commercially available. For example, FMOC amino acids are available from a variety of sources. The conversion of these compounds to the second component pieces of this invention may be readily achieved by activation of the carboxylic acid group of the N-protected amino acid. Suitable activated carboxylic acid groups include acid halides where X is a halide such as chloride or bromide, acid anhydrides where X is an acyl group such as acetyl, reactive esters such as an N-hydroxysuccinimide esters and p-nitrophenyl esters, and other activated intermediates such as the active intermediate formed in a coupling reaction using a carbodiimide such as dicyclohexylcarbodiimide (DCC). Similarly, the corresponding azido derivative may be prepared by known techniques. In a preferred embodiment, X is hydroxyl for HATU (0-(7-azabenzotriaol-1-yl)-1,1,3,3-tetramethyluronium hexafluorophosphate) coupling, or is fluorine for silicon mediated coupling.

C. Representative Third Component Pieces

A representative third component piece of this invention is an α,β-unsaturated carboxylic acid or derivative thereof having the following structure 3:

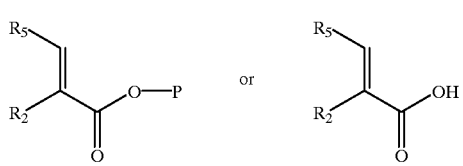

where $R_2$ and $R_5$ are as defined above, and P is a carboxylic acid protective group such as a methyl or t-butyl group. Such third component pieces may be obtained commercially, or synthesized from the commercially available aldehyde and the appropriate phosphorusylide according to the following reaction scheme:

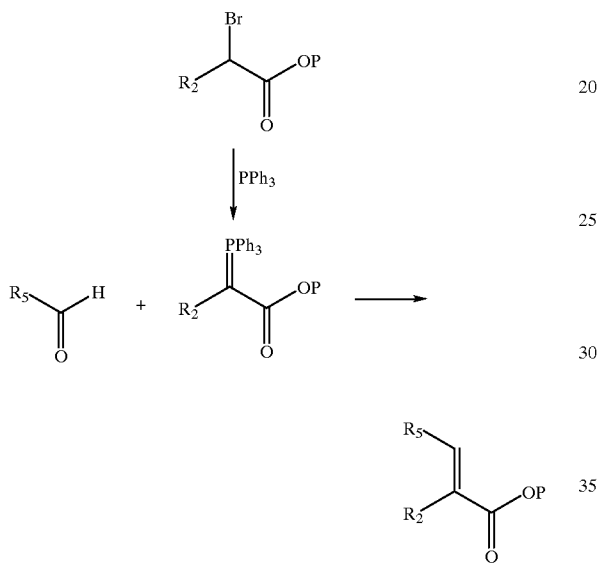

(see, Wadsworth and Emmons, *Org. Syn.* 45:44, 1965).

D. Representative Fourth Component Pieces

A representative fourth component piece of this invention is a primary amine having the following structure 4:

$R_1-NH_2$      4 where $R_1$ is as defined above. Suitable fourth component pieces are commercially available from a variety of sources. Alternatively, the fourth component pieces may be readily prepared by standard organic synthetic techniques commonly utilized for the synthesis of primary amines.

Example 2

Combined First-Second Intermediates: The Coupling of First and Second Component Pieces The coupling of the component pieces to produce the reverse-turn mimetics of the present invention generally involve the formation of amide bonds. The amide bonds which link the pieces may be formed by standard synthetic peptide techniques and may be performed by either liquid or solid phase synthesis.

The coupling of the first and second component pieces provides, after deprotection, a combined first-second intermediate having the following structure 1-2:

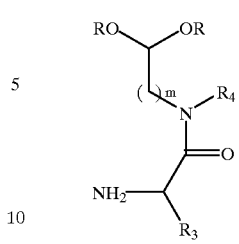

where R, $R_3$, and $R_4$ are as described above (in this example, R" of structure (I) is/are hydrogen).

The preparation of a combined first-second intermediate is accomplished by amide bond formation between the amine of a first component piece 1 and the activated carboxylic acid group of a second component piece 2 followed by N-deprotection. The synthesis of a representative combined first-second intermediate is depicted schematically below.

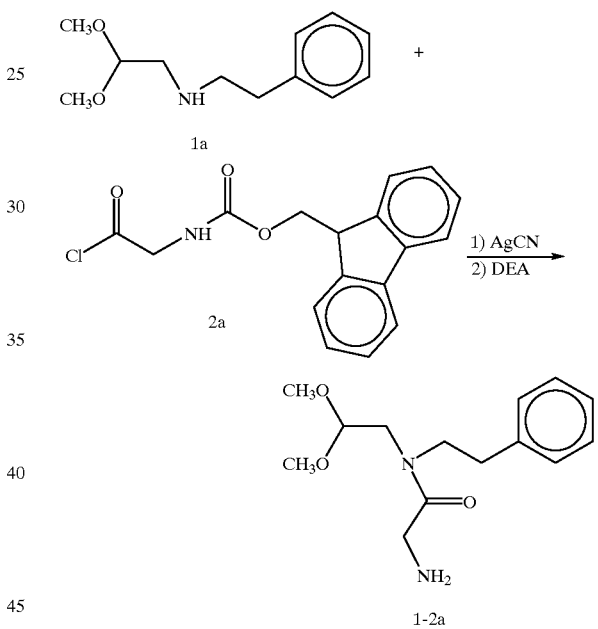

In the procedure, to 650 mg (3.17 mmol) first component piece 1a prepared as described in Example 1A and 1 g (3.17 mmol) FMOC-glycine chloride, 2a, 10 ml freshly distilled benzene in a 25 ml argon charged round bottom flask was added 937 mg (7 mmol) silver cyanide (AgCN), and the resulting reaction mixture was stirred vigorously for 48 hrs. The reaction was diluted to 25 ml w/ethyl acetate and filtered through a Celite plug. Volatiles were removed under reduced pressure and the residue was chromatographed using 20:80 ethyl acetate:hexane as the mobile phase over flash grade silica gel to yield 1.1 g (71%) of an amorphous solid.

To 400 mg (0.82 mmol) of the amorphous solid in 5 ml acetonitrile was added 1 ml diethylamine (DEA) dropwise and the resulting reaction mixture was stirred at room temperature for 2 hrs. The volatiles were removed under reduced pressure and the residue was chromatographed using 5% methanol saturated with ammonia 95% dichloromethane as the mobile phase over flash grade silica gel to yield 207 mg (95%) of a combined first-second intermediate, 1-2a, as a thick colorless oil.

Example 3

Combined Third-Fourth Intermediates: The Coupling of Third and Fourth Component Pieces The coupling of a third component piece with a fourth component piece provides a combined third-fourth intermediate. The combined third-fourth component piece is produced by amine bond formation resulting from the conjugate addition of the amine group of a fourth component piece 4 to the α,β-unsaturated carbonyl group of a third component piece 3.

The coupling of third and fourth component pieces provides, after deprotection, a combined third-fourth intermediate having the following structure 3-4:

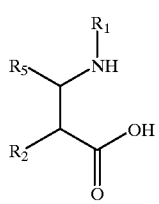

3-4 where $R_1$, $R_2$, and $R_5$ are as described above (in this example, n of structure (I) is O).

The preparation of a combined third-fourth intermediate is accomplished by amine bond formation between the primary amino group of a fourth component piece 4 and α,β-unsaturated carbonyl group of a third component piece 3 followed by O-deprotection. The synthesis of a representative combined third-fourth intermediate is depicted schematically below.

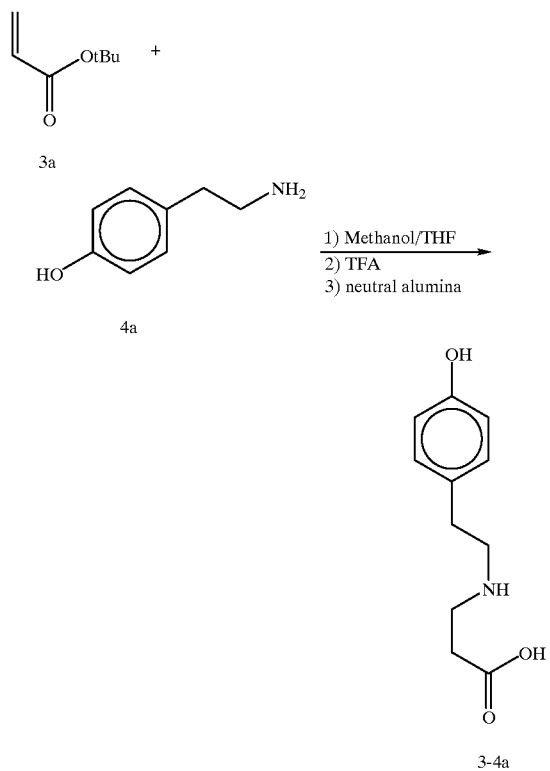

In the procedure, to 5 g of tyramine suspended in 40 ml freshly distilled tetrahydrofuran (THF) in an argon charged, 250 ml round-bottom flask was added methanol sufficient to dissolve the suspension. To the resulting solution was added 5.3 ml (4.67 g, 36.4 mmol) of t-butylacrylate dropwise over the course of 5 min, and the resulting reaction mixture was stirred overnight at room temperature. An additional 2 ml of t-butylactylate was added to consume the remaining starting material and the reaction was stirred an additional 4 hrs. Volatiles were removed under reduced pressure and the residue was chromatographed using 95:5 dichloromethane:ammonia saturated methanol:$NH_3$/MeOH as the mobile phase over flash grade silica gel to yield 6.6 g (68%) of the ester, a colorless oil which solidified upon overnight refrigeration. To a solution of 1 gram (3.77 mmol) of the ester in 20 ml dichloromethane at 0° C. was added 80 ml of cold trifluoroacetic acid (TFA) and the resulting reaction mixture was stirred with warming to room temperature over the course of 24 hrs. Volatiles were removed under reduced pressure to yield 950 mg of a clear oil. The end product was dissolved in 95:5 dichloromethane:methanol and slowly filtered through a pad of neutral alumina. Volatiles were removed from the filtrate to yield 750 mg of 3-4a as an amorphous solid.

Example 4

Combined First-Second-Third-Fourth Intermediates: The Coupling of Combined First-Second and Third-Fourth Intermediates The coupling of a combined first-second intermediate with a combined third-fourth intermediate provides a combined first-second-third-fourth intermediate. The combined first-second-third-fourth intermediate is produced by amide bond formation resulting from the coupling of the amine group of a combined first-second intermediate 1-2 to the carboxylic acid group of a combined third-fourth intermediate 3-4. The combined first-second-third-fourth intermediate has the following structure 1-2-3-3-4:

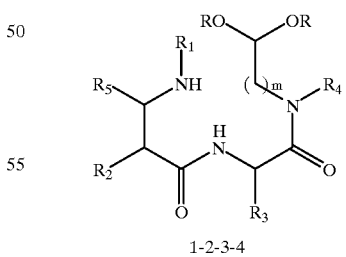

1-2-3-4 where R, $R_1$, $R_2$, $R_3$, $R_4$ and $R_5$ are as described above.

The synthesis of a representative combined first-second-third-fourth intermediate is depicted schematically below.

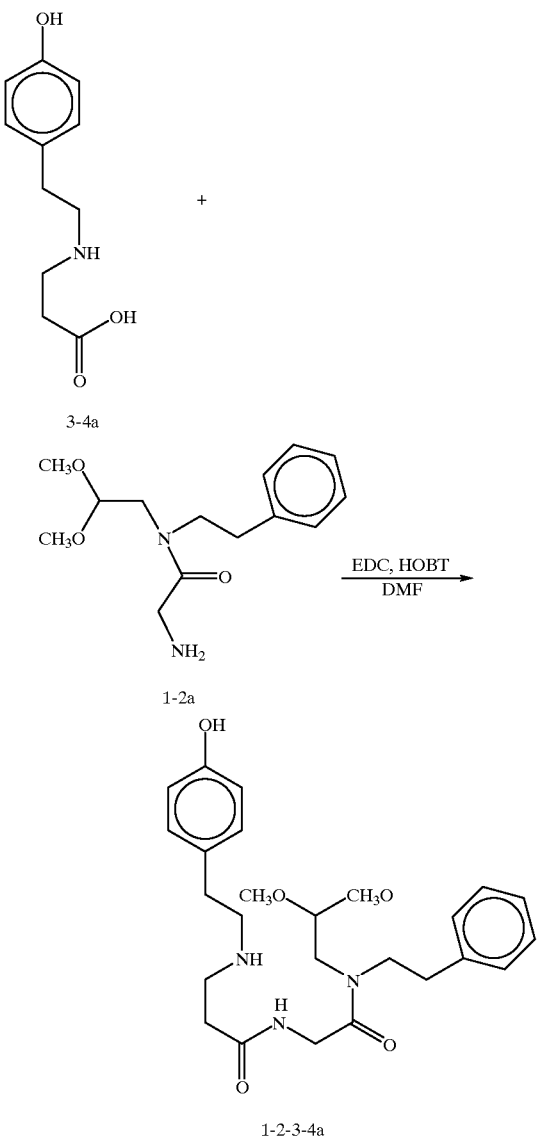

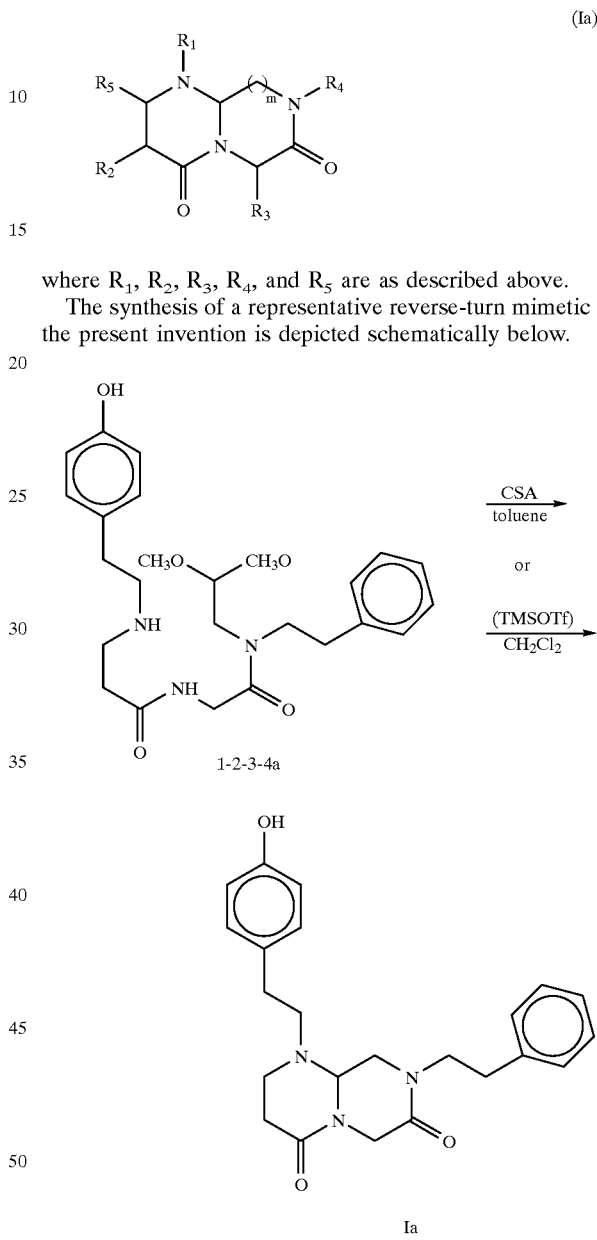

In the procedure, 212 mg (1.0 mmol) 3-4a, 270 mg (1.01 mmol) 1-2a, and 136 mg (1.01 mmol) 1-hydroxybenzotriazole hydrate (HOBT) were dissolved in 10 ml dimethylformamide (DMF) and cooled to 0° C. To this solution was added 290 mg (1.52 mmol, 1.5 eq) 1-(3-dimethylaminopropyl)-3-ethylcarbodiimide (EDC) and the resulting reaction mixture was stirred and warmed to room temperature over the course of 24 hours. The DMF was removed under reduced pressure and the residue was redissolved in 200 ml ethyl acetate. The ethyl acetate layer was washed with saturated aqueous sodium bicarbonate, water, and dried over anhydrous sodium sulfate. Volatiles were removed under reduced pressure and the residue was chromatographed using 95:5 dichloromethane: ammonia saturated methanol as eluent over flash-grade silica gel to yield 310 mg (0.68 mm 67%) 1-2-3-4a as a thick colorless oil.

Example 5

The Synthesis of a Representative Reverse-Turn Mimetic: Cyclization of a Combined First-Second-Third-Fourth Intermediate The cyclization of a combined first-second-third-fourth intermediate provides a reverse-turn mimetic of the present invention. The combined first-second-third-fourth intermediate 1-2-3-4 is cyclized by treatment with camphorsulfonic acid (CSA) or, in a preferred embodiment, TMSOTF (at 0° C.) to provide a reverse-turn mimetic having the following structure (Ia):

where $R_1$, $R_2$, $R_3$, $R_4$, and $R_5$ are as described above.

The synthesis of a representative reverse-turn mimetic of the present invention is depicted schematically below.

In the procedure, 0.5 g (2.4 mmol) camphorsulfonic acid (CSA) was azeotroped with 3–15 ml portions of freshly distilled toluene and dried under vacuum at 40° C. for 3 hrs in a 100 ml round-bottom flask equipped with a reflux condenser. Then 20 ml of freshly distilled toluene was added and the CSA solution was heated to a vigorous reflux. To this refluxing CSA solution was added a solution of 50 mg (0.11 mmol) 1-2-3-4a in 20 ml of freshly distilled toluene by syringe pump over the course of 1 hr. The resulting reaction mixture was refluxed for 12 hrs, cooled to room temperature and diluted to 200 ml ethylacetate. The organic layer was washed with 2–75 ml portions of saturated aqueous sodium bicarbonate, 75 ml saturated aqueous sodium chloride, and dried over anhydrous sodium sulfate. Volatiles were removed under reduced pressure to yield 22 mg of Ia as a glassine solid. The crude product was triturated with 50/50 diisopropyl ether:hexane to remove non-polar impurities. The solid was then dissolved in dichloromethane and filtered to remove polar impurities. The residue upon evaporation was dried in vacuo for 24 hrs.

Example 6

The Synthesis of a Representative Reverse-Turn Mimetic Salt

The reverse-turn mimetics of the present invention are nitrogen bases and may, therefore, be converted to their corresponding salts by treatment with various acids. In this example, the preparation of a representative salt of a reverse-turn mimetic is described.

The 2,4-dinitrobenzoic acid salt of reverse-turn mimetic Ia, prepared as described in Example 5, was obtained by treatment of the reverse-turn mimetic with the acid in aqueous methanol. In the procedure, 5 mg (12.7 μmol) Ia was dissolved in 3 ml of 80/20 methanol:water and cooled to 0° C. To this solution was added 2.70 mg (12.7 μmol, 1.0 eq) 2.4 dinitrobenzoic acid, and the resulting solution stirred until it became homogenous. Volatiles were removed under reduced pressure and the residue was dried in vacuo for 24 hrs. The residue was taken up in warm water and filtered to remove insoluble impurities. The salt was then lyophilized.

Example 7

Activity of a Representative Reverse-Turn Mimetic in Opioid Receptor Binding

In this example, the binding activity of a representative reverse-turn mimetic to the delta (δ) and mu (μ) opioid receptors is described. In these methods, the binding of the 2,4-dinitrobenzoic acid salt of reverse-turn mimetic of structure Ia, prepared as described in Example 6, was evaluated in competitive radioligand binding assays.

A. Opiate (δ) Binding Activity

In this method, membranes were prepared from whole brains of male guinea pigs and equilibrated with 2 nM [$^3$H]DPDPE (D-pen$^3$, D-pen$^5$) enkephalin for 1 hour at 4° C. after which test substances were added and incubated for 4 hours at 25° C. Non-specific binding was determined in the presence of 0.3 μM naltrindole. Bound [$^3$H]DPDPE was separated from free radioligand by rapid filtration through glass fiber filtermats and subsequently washed 3 times. Filtermats were then counted in the LKB Betaplate to determine specifically bound [$^3$H]DPDPE. (See Mosberg et al., "Structural Requirements for δ Opiate Receptor Binding," *Molec. Pharmacol.* 31:599–602, 1987.)

TABLE 2

Effect of Reference Compounds on [$^3$H]DPDPE Bound (2nM)

| Compound | IC$_{50}$ (nM) | Ki (nM) | Hill Coefficient |
|---|---|---|---|
| DAMGO | 4,800 | 1,200 | 1.08 |
| DPDPE | 5.5 | 1.3 | 0.86 |
| Naltrindole | 0.63 | 0.20 | 0.53 |
| U-50488 | 53,000 | 16,000 | 0.73 |

In this assay, the radioligand, [$^3$H]DPDPE, was determined to have a K$_d$=0.65 nM with a B$_{max}$=12.6 fmol/mg protein and a specific binding of 60%. At a concentration of 10 μM, the 2,4-dinitrobenzoic acid salt of reverse-turn mimetic Ia was found to inhibit radioligand binding at the 60% level, and exhibited a K$_i$=1.7±0.3 μM and an IC$_{50}$=6.9±1.2 μM. These results are presented in FIG. 1 (○) which depicts the % inhibition of radioligand binding as a function of reverse-turn mimetic Ia concentration. These results demonstrate that reverse-turn mimetic Ia, in particular, and the reverse-turn mimetics of the present invention, in general, effectively inhibit binding to the δ opiate receptor, and possesses analgesic activity.

B. Opiate (μ) Binding Activity

In this method, membranes were prepared from whole brains of male guinea pigs and incubated with 2 nM [$^3$H]DAMGO (D-Ala$^2$, N-methyl-phe$^4$, gly-ol$^5$)-enkephalin) for 2 hours at 25° C. Non-specific binding was determined in the presence of 0.5 μM DAMGO. Bound [$^3$H]DAMGO was separated from free radioligand by rapid filtration through glass fiber filtermats and subsequently washed 3 times. Filtermats were then counted in the LKB Betaplate to determine specifically bound [$^3$H]DAMGO. (See Patricia et al., "Pharmacological profiles of fentanyl analogs at μ, δ and κ opiate receptors," *Eur. J. Pharmacol.* 213:219–225, 1992.)

TABLE 3

Effect of Reference Compounds on [$^3$H]DAMGO Bound (2nM)

| Compound | IC$_{50}$ (nM) | Ki (nM) | Hill Coefficient |
|---|---|---|---|
| DAMGO | 6.5 | 0.59 | 0.92 |
| DPDPE | 4.0 | 0.37 | 1.32 |
| Fentanyl | 14 | 1.2 | 0.99 |
| Naloxone | 9.3 | 0.76 | 1.09 |
| Naltrindole | 27 | 2.5 | 0.98 |
| Norbinaltorphimine | 280 | 26 | 1.13 |
| U-50488 | 6.1 | 0.59 | 0.70 |

In this assay, the radioligand, [$^3$H]DAMGO, was determined to have a K$_d$=0.27 nM with a B$_{max}$=8.7 pmol/mg protein and a specific binding of 70%. At a concentration of 10 μM, the 2,4-dinitrobenzoic acid salt of reverse-turn mimetic Ia inhibited radioligand binding at the 64% level, and exhibited a K$_i$=0.64±0.08 μM and an IC$_{50}$=5.4±0.7 μM. These results are presented in FIG. 1 (●) which depicts the % inhibition of radioligand binding as a function of reverse-turn mimetic Ia concentration. These results demonstrate that reverse-turn mimetic Ia, in particular, and the reverse-turn mimetics of the present invention, in general, effectively inhibit binding to the μ opiate receptor, and possesses analgesic activity.

Example 8

In Vitro Activity of a Representative Reverse-Turn Mimetic for Analgesic Activity In this example, the in vivo activity of a representative reverse-turn mimetic as an analgesic agent is presented. The 2,4-dinitrobenzoic acid salt of the reverse-turn mimetic of structure Ia, prepared as described in Example 6 (hereinafter referred to as "test compound"), was utilized in the mouse tail flick assay (PanLabs, Pharmascreen Test No. 10402A). In this assay, the time required to elicit a tail-flick response to radiant heat pain stimulus in a group of mice is measured as the pain threshold response.

Groups of five (3 test groups+1 saline control +1 morphine positive control) male ICR mice weighing 22 (±2) grams each were used. Each of these animals were preselected and elicited a tail flick response within 6–7.5 seconds after a focused beam of radiant heat was focused on the middle dorsal surface of the animal's tail. Specific amounts of the test compound (i.e., 10, 30 and 100 μg) were dissolved in 5 microliters (5μl) saline containing 6% DMSA and administered intracerebroventricularly (ICV) to each animal. A saline-only solution was used as a negative control, with an ICV injection of 10 μg/5 μl/animal of morphine serving as a positive control.

At one minute post-ICV injection, the groups of mice were measured for tail flick response, with a maximum cut-off time of 15 seconds. The mean of the response time for each treatment groups was calculated for a comparison between pre-treatment ("0 time") and 1 minute post-treatment l("1 min."). Prolongation 1 minute post-treatment of over 50% ("% Prolong.") was considered significant activity. The results of this experiment are presented in Table 4, and demonstrate that the test compound had significant analgesic activity (i.e., approximately 10%–15% the potency of morphine).

TABLE 4

In Vivo Tail Flick Assay

| Compound | Dose/5 μl | 0 Time | 1 Min. | % Prolong. |
|---|---|---|---|---|
| Saline | 0 | 6.9 | 6.7 | — |
| | | 6.9 | 7.5 | — |
| | | 6.1 | 6.2 | — |
| | | 6.5 | 6.3 | — |
| | | Avg. = 6.6 | Avg. = 6.7 | 2% |
| Morphine | 10 μg | 7.5 | >15 | — |
| | | 6.3 | >15 | — |
| | | 7.2 | >15 | — |
| | | 6.8 | >15 | — |
| | | Avg. = 7.0 | Avg. > 15 | 100% |
| Test Compound | 100 μg | 6.5 | >15 | — |
| | | 6.3 | >15 | — |
| | | 6.5 | >15 | — |
| | | 6.8 | >15 | — |
| | | Avg. = 6.5 | Avg. > 15 | 100% |
| | 30 μg | 6.5 | >15 | — |
| | | 6.7 | 7.2 | — |
| | | 7.2 | 6.3 | — |
| | | 6.3 | >15 | — |
| | | Avg. = 6.7 | Avg. > 15 | 63% |
| | 10 μg | 6.5 | 7.5 | — |
| | | 7.2 | 7.5 | — |
| | | 6.9 | 6.7 | — |
| | | 6.2 | 6.8 | — |
| | | Avg. = 6.7 | Avg. 7.1 | 6% |

It will be appreciated that, although specific embodiments of the invention have been described herein for the purposes of illustration, various modifications may be made without departing from the spirit and scope of the invention. Accordingly, the invention is not limited except by the appended claims.

I claim:

1. A compound having the structure:

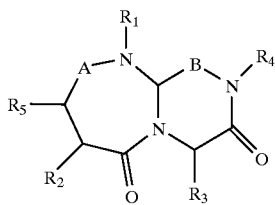

wherein

A is —(CHR')$_n$—;

B is —(CHR'')$_m$—;

n is 0, 1 or 2;

m is 1, 2 or 3;

R', R'', $R_2$, $R_3$ and $R_5$ are the same or different and each occurrence of the same is independently selected from the group consisting of an amino acid side chain moiety, an amino acid side chain derivative, a linker and a solid support; and $R_1$ and $R_4$ represent the remainder of the compound, wherein $R_1$ and $R_4$ are the same or different and independently selected from the group consisting of a moiety, agent, compound, support, molecule, linker, amino acid, peptide and protein;

with the proviso that no more than one of R', R'', $R_1$, $R_2$, $R_3$, $R_4$ or $R_5$ is a solid support.

2. The compound of claim 1 wherein R' is hydrogen.

3. The compound of claim 1 wherein R'' is hydrogen.

4. The compound of claim 1 wherein n=0.

5. The compound of claim 1 wherein m=1 or 2.

6. The compound of claim 1 wherein $R_5$ is hydrogen.

7. The compound of claim 1 wherein n=0, R'' and $R_5$ are hydrogen, and the compound has the structure:

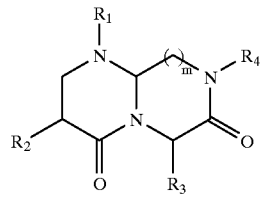

8. The compound of claim 7 wherein $R_2$ and $R_3$ are the same or different and independently selected from an amino acid moiety or derivative thereof.

9. The compound of claim 7 wherein $R_4$ is joined to a solid support.

10. The compound of claim 1 wherein n=0, R'' and $R_5$ are hydrogen, m=1, and the compound has the structure:

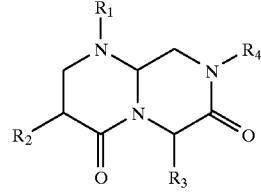

11. The compound of claim 10 wherein $R_2$ and $R_3$ are the same or different and independently selected from an amino acid moiety or derivative thereof.

12. The compound of claim 10 wherein $R_4$ is joined to a solid support.

13. A library of compounds, comprising at least one compound of any one of claims 1 through 12.

14. A method of identifying a biologically active compound, comprising contacting the library of claim 13 with a target to detect or screen the biologically active compound.

* * * * *